United States Patent
Winslow et al.

(10) Patent No.: US 10,588,752 B2
(45) Date of Patent: Mar. 17, 2020

(54) MODULAR BONE MODEL

(71) Applicant: Biomet Manufacturing, LLC, Warsaw, IN (US)

(72) Inventors: Nathan A. Winslow, Warsaw, IN (US); Clinton E. Kehres, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/471,369

(22) Filed: Mar. 28, 2017

(65) Prior Publication Data

US 2017/0281355 A1    Oct. 5, 2017

Related U.S. Application Data

(60) Provisional application No. 62/314,450, filed on Mar. 29, 2016.

(51) Int. Cl.
*A61F 2/40* (2006.01)
*G09B 23/34* (2006.01)
(Continued)

(52) U.S. Cl.
CPC ........ *A61F 2/4014* (2013.01); *A61F 2/30771* (2013.01); *A61F 2/30942* (2013.01);
(Continued)

(58) Field of Classification Search
CPC ............ A61F 2/4014; A61F 2002/4018; A61F 2002/4037; A61F 2/4081; A61F 2/4684; A61F 2/30942
See application file for complete search history.

(56) References Cited

U.S. PATENT DOCUMENTS 5,358,526 A * 10/1994 Tornier ................. A61F 2/4014
623/19.14
5,507,817 A * 4/1996 Craig .................... A61F 2/4014
606/309
(Continued)

FOREIGN PATENT DOCUMENTS

WO    WO-2008109751 A1    9/2008
WO    WO-2012003175 A1    1/2012
(Continued)

OTHER PUBLICATIONS

"International Application Serial No. PCT/US2017/024475, International Search Report dated Jun. 7, 2017", 6 pgs.
(Continued)

*Primary Examiner* — Alvin J Stewart
(74) *Attorney, Agent, or Firm* — Schwegman Lundberg & Woessner, P.A.

(57) ABSTRACT

A modular bone model can include a bone component and an implant component that can be positioned on the bone component. The implant component can be shaped and sized to correspond to a head component of a medical implant to simulate an articulating surface of the head component. Similarly, the bone component can be shaped to simulate a natural bone to which the medical implant can be mounted. Alternatively, the head component of the medical implant can be mounted directly to the bone component to simulate the mounting on the natural bone.

19 Claims, 8 Drawing Sheets

(51) Int. Cl.
*A61F 2/30* (2006.01)
*G09B 23/32* (2006.01)
*A61F 2/46* (2006.01)

(52) U.S. Cl.
CPC ............ *A61F 2/4684* (2013.01); *G09B 23/32* (2013.01); *G09B 23/34* (2013.01); *A61F 2/4003* (2013.01); *A61F 2002/3052* (2013.01); *A61F 2002/30492* (2013.01); *A61F 2002/30495* (2013.01); *A61F 2002/30604* (2013.01); *A61F 2002/30672* (2013.01); *A61F 2002/4018* (2013.01)

(56) References Cited

U.S. PATENT DOCUMENTS

| | | | | |
|---|---|---|---|---|
| 5,702,486 | A * | 12/1997 | Craig | A61F 2/4014 623/19.14 |
| 5,910,171 | A * | 6/1999 | Kummer | A61F 2/4014 623/18.11 |
| 6,197,062 | B1 * | 3/2001 | Fenlin | A61F 2/4014 623/19.12 |
| 6,197,063 | B1 * | 3/2001 | Dews | A61F 2/4014 623/19.14 |
| 6,530,957 | B1 * | 3/2003 | Jack | A61F 2/4014 623/19.14 |
| 6,626,946 | B1 * | 9/2003 | Walch | A61F 2/40 623/19.11 |
| 6,676,705 | B1 * | 1/2004 | Wolf | A61F 2/4014 623/19.14 |
| 6,719,799 | B1 * | 4/2004 | Kropf | A61F 2/4014 623/19.12 |
| 7,416,565 | B1 | 8/2008 | Al-turaikl | |
| 8,052,758 | B1 * | 11/2011 | Winslow | A61F 2/4014 623/22.42 |
| 9,770,334 | B2 * | 9/2017 | Wiley | A61F 2/30734 |
| 9,883,948 | B2 * | 2/2018 | Chavarria | A61F 2/4014 |
| 9,918,854 | B2 * | 3/2018 | Bonin, Jr. | A61F 2/4637 |
| 2001/0053935 | A1 * | 12/2001 | Hartdegen | A61F 2/4014 623/19.12 |
| 2002/0156534 | A1 * | 10/2002 | Grusin | A61F 2/4014 623/19.14 |
| 2004/0064187 | A1 * | 4/2004 | Ball | A61F 2/4014 623/19.11 |
| 2004/0143335 | A1 * | 7/2004 | Dews | A61F 2/4014 623/19.14 |
| 2005/0033443 | A1 * | 2/2005 | Blatter | A61F 2/4014 623/19.14 |
| 2005/0203634 | A1 * | 9/2005 | Bassik | A61F 2/36 623/22.42 |
| 2007/0162140 | A1 * | 7/2007 | McDevitt | A61F 2/4014 623/18.11 |
| 2007/0173945 | A1 * | 7/2007 | Wiley | A61F 2/30734 623/19.13 |
| 2008/0140211 | A1 * | 6/2008 | Doubler | A61F 2/4014 623/19.14 |
| 2008/0228281 | A1 * | 9/2008 | Forrer | A61F 2/4014 623/19.12 |
| 2010/0076561 | A1 * | 3/2010 | Emmanuel | A61F 2/4014 623/19.11 |
| 2011/0118846 | A1 * | 5/2011 | Katrana | A61F 2/4014 623/19.13 |
| 2011/0224673 | A1 * | 9/2011 | Smith | A61F 2/4003 606/87 |
| 2013/0173006 | A1 * | 7/2013 | Duport | A61F 2/4003 623/19.11 |
| 2013/0197652 | A1 * | 8/2013 | Ekelund | A61F 2/30728 623/19.14 |
| 2013/0230838 | A1 | 9/2013 | Iannotti et al. | |
| 2014/0114425 | A1 * | 4/2014 | Ekelund | A61F 2/30728 623/19.14 |
| 2014/0121709 | A1 * | 5/2014 | Gonzalez-Hernandez | A61F 2/4003 606/286 |
| 2014/0180424 | A1 * | 6/2014 | Dickerson | A61F 2/3609 623/19.12 |
| 2014/0277521 | A1 * | 9/2014 | Chavarria | A61F 2/4014 623/19.13 |
| 2014/0288657 | A1 * | 9/2014 | Lederman | A61F 2/4014 623/19.14 |
| 2016/0324648 | A1 * | 11/2016 | Hodorek | A61F 2/4003 |
| 2017/0020677 | A1 * | 1/2017 | McElhaney, Jr. | A61F 2/4684 |
| 2017/0056187 | A1 * | 3/2017 | Humphrey | A61F 2/4014 |
| 2017/0128220 | A1 * | 5/2017 | Iannotti | A61F 2/4014 |
| 2017/0202685 | A1 * | 7/2017 | Rao | A61F 2/4684 |
| 2017/0340449 | A1 * | 11/2017 | Deransart | A61F 2/4014 |
| 2017/0367835 | A1 * | 12/2017 | Faccioli | A61F 2/4014 |
| 2018/0064546 | A1 * | 3/2018 | Rosa | A61F 2/4014 |

FOREIGN PATENT DOCUMENTS

| | | |
|---|---|---|
| WO | WO-2014070681 A1 | 5/2014 |
| WO | 2017172717 | 10/2017 |

OTHER PUBLICATIONS

"International Application Serial No. PCT/US2017/024475, Written Opinion dated Jun. 7, 2017", 6 pgs.

"European Application Serial No. 17717032.1, Response filed May 24, 2019 to Office Action dated Nov. 14, 2018", 16 pgs.

"European Application Serial No. 17717032.1, Communication Pursuant to Article 94(3) EPC dated Oct. 28, 2019", 4 pages.

* cited by examiner

MODULAR BONE MODEL

CLAIM OF PRIORITY

This patent application claims the benefit of priority, under 35 U.S.C. Section 119(e), to Nathan A. Winslow et al., U.S. Patent Application Ser. No. 62/314,450, entitled "MODULAR BONE MODEL," filed on Mar. 29, 2016, each of which is hereby incorporated by reference herein in its entirety.

TECHNICAL FIELD

This document pertains generally, but not by way of limitation, to bone models for trialing medical implants for arthroplasty surgical procedures.

BACKGROUND

Arthroplasty surgical procedures repair or replace the articulating surfaces of a joint where the bone surfaces defining the articulating surfaces have become damaged. Arthroplasty surgery typically involves resection of the damaged bone structure and installation of one or more medical implants on a prepared region on the remaining bone to replace or supplement the natural articulating surfaces of the damaged bone. A primary consideration during arthroplasty procedures is mounting the medical implant to the remaining bone or a mounting implant attached to the bone to replicate the natural articulating surfaces or positioning the articulating surface to provide a sufficiently tight joint fit. Improper positioning or sizing of the implant articulating surface can cause irregular joint movement or insufficient contact with the corresponding articulating surface, which can damage or irregularly wear the remaining bone.

In order to aid in the fitting of the medical implant, medical kits for arthroplasty surgery often include a medical implant that can be fitted with various differently sized and/or configured head components. Each head component can have a differently shaped articulating surface. During an arthroplasty surgery, the surgeon selects the appropriately sized and configured head component to provide the desired articulating surface. After preparing a mounting surface for the medical component on the remaining bone, the surgeon typically "trials" the medical implant by positioning different head components on the mounting surface and in different orientations and offsets until the best articulating surface and orientation is identified. While trialing different head components can improve the fit of the articulating surface, the trialing can considerably extend the surgical procedure and creates a risk of complications resulting from repeatedly positioning and exchanging head components.

OVERVIEW

The present inventors have recognized, among other things, that a problem to be solved can include the trialing of different head components during surgical procedures to determine the head component providing the appropriate articulating surface for repairing a joint. In an example, the present subject matter can provide a solution to this problem, such as by providing a modular bone model having a bone component and an implant component that can be positioned on the bone component. The implant component can be shaped and sized to correspond to a head component of a medical implant to simulate an articulating surface of the head component. The bone component can be shaped to simulate a natural bone to which the medical implant can be mounted. The bone component can be shaped to correspond to the In an example, the bone component can include a mounting surface simulating a prepared mounting region of the natural bone after the bone has been resected in preparation for mounting the medical implant.

The implant component can be positioned on the bone component to simulate the position of the head component mounted on a prepared surface of the bone or a mounting surface of a mount implant, thereby allowing pre-operation trialing of the head component. In an example, a plurality of implant components, each corresponding to a different head component, can be provided for trialing different head components and corresponding articulating surface. The pre-operation trialing reduces the operating time and the corresponding risk of complications created in procedure trialing.

In an example, the bone component can include at least one positioning feature for positioning the implant component on the mounting surface. The implant component can include a corresponding alignment feature that engages the positioning feature to position the implant component to simulate the positioning of the corresponding head component. In an example, the alignment feature can adjustably engage the positioning feature to allow offsetting of the implant component on the mounting surface. In this configuration, surgeons can trial different offset positions for the modular component pre-operation in order to order to determine if the offset improves the fit of the articulating surface.

In an example, the bone component can include a releasable locking feature for exchanging various bone components for trialing various articulating surfaces. The releasable locking feature can comprise a flexible, resilient material permitting removing and exchanging bone components for rapid trialing of the bone components.

In an example, the releasable locking feature can be configured to interface with an engagement feature of a head component allowing the head component to be mounted to the bone component for further pre-operative trialing of the head component. In this configuration, the bone model can be provided with the head component attached to the bone component rather than an implant component. The bone model kit with the head component can allow surgeons make final trialing of potential offsets of the head component immediately prior to mounting to the bone. In at least one example, the releasable locking feature can be configured to be cut with a scalpel or tool to separate the head component from the bone component during the operation. In this configuration, the bone model kit with the interchangeable attached can be provided with the head component attached to the bone component avoid confusion during the operation or loss of either the head component or the bone component during transport.

In an example, a method can be provided for trialing a medical implant having a head component defining an articulating surface. The method can include providing a bone component shaped to simulate natural bone prepared to receive the medical implant. The method can also include providing an implant component shaped and sized such that an articulating surface of the implant component corresponds to the articulating surface of the head component. The method can also include adjustably positioning the implant component on the bone component to simulate positioning of the medical implant on the natural bone and the corresponding position of the articulating surface.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
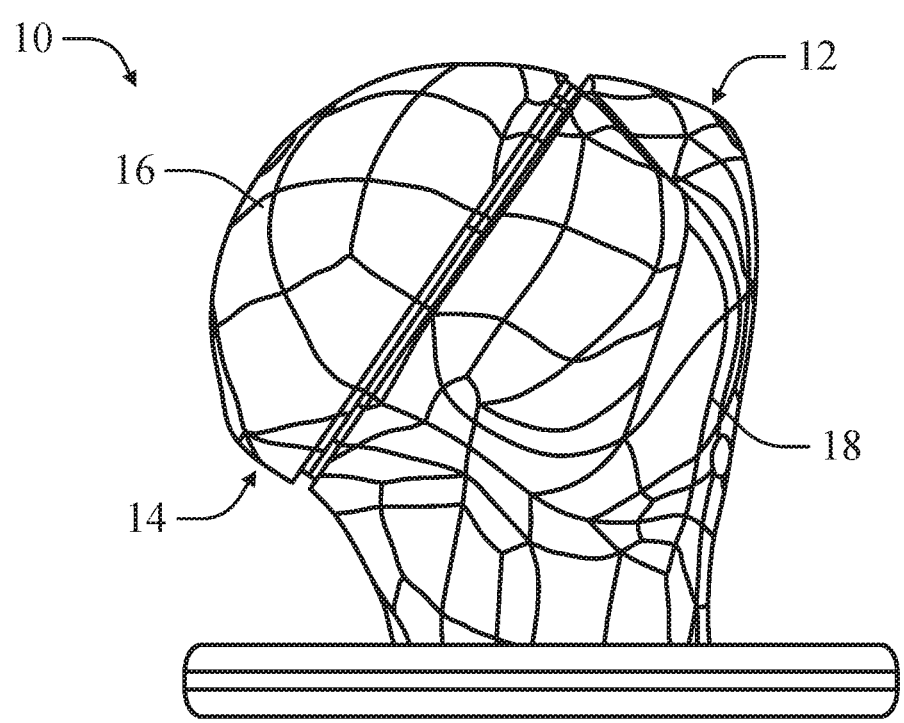
FIG. 1 is a side view of a bone model according to an example of the present disclosure.
Figure 2:
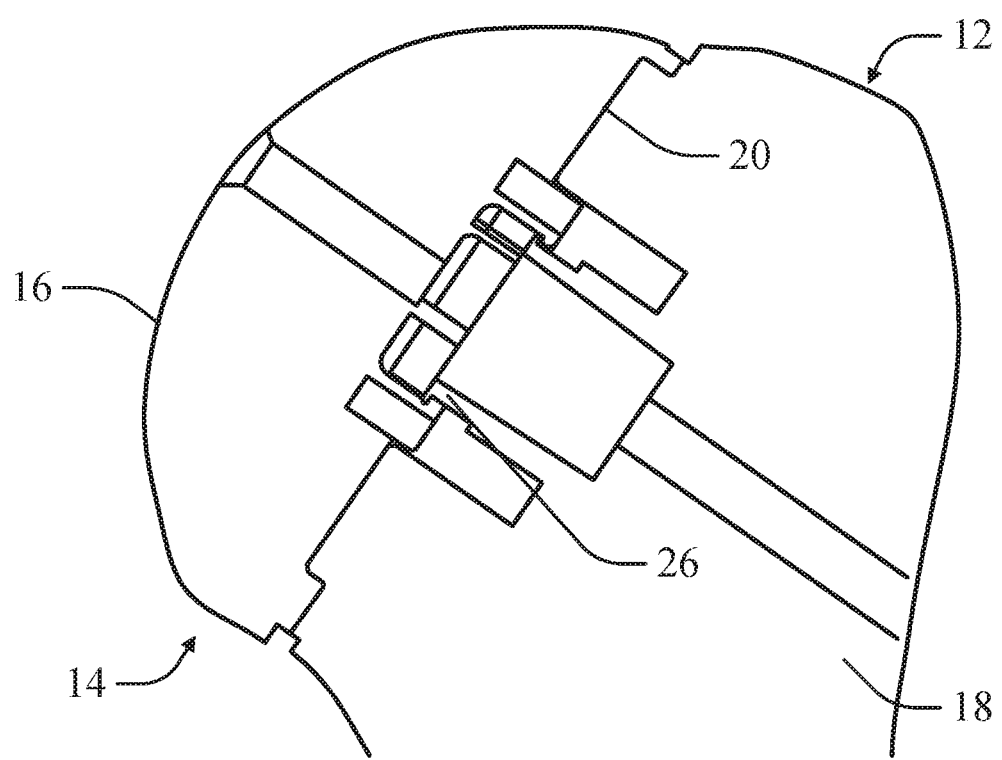
FIG. 2 is a partial cross-sectional side view of the bone model depicted in FIG. 1 according to an example of the present disclosure.

As illustrated in FIGS. 1-2, a bone model 10, in an example, can include a bone component 12 and an implant component 14, wherein the implant component 14 can be positioned on the bone component 12. The bone component 12 can include a mounting surface 20 simulating a prepared surface on a bone for receiving a medical implant for repairing or supplementing a natural articulating surface. In an example, the mounting surface 20 of the bone component 12 can simulate a mounting surface of a mounting implant inserted into the bone for receiving the medical implant having a simulated articulating surface. The implant component 14 can approximate the shape and size of a head component of the medical device, such that the implant component 14 defines an articulating surface 16 approximating the articulating surface of the corresponding head component. The implant component 14 can be positioned on the bone component 12 to simulate the positioning of the head component when mounted on the bone to allow pre-operation trialing for determining the appropriate implant component 14 and corresponding head component.

As depicted in FIGS. 1-2, the bone model 10 is configured for shoulder arthroplasty procedures. Specifically, the bone component 12 is shaped to simulate the shape and size of a humerus having a prepared mounting surface or a humerus having a mounting implant inserted into the humerus, wherein the mounting implant provides an artificial mounting surface. In an example, the bone model can be provided measurements and modeling provided by x-rays, gamma rays, magnetic resonance and other non-invasive or damaging imaging techniques. Similarly, the implant component 14 approximates the size and shape of a head component of a humeral implant such that the articulating surface 16 of the implant component 14 simulates the articulating surface of the head. The humeral bone model 10 is intended to be demonstrative and not intended to be limiting. It is contemplated that the bone model 10 can be used to simulate a variety of different arthroplasty implant procedures including, but not limited to arthroplasty procedures for complete or partial replacement of the articulating surfaces of hip joints, knee joints, shoulder joints, and finger joints.

Figure 3:
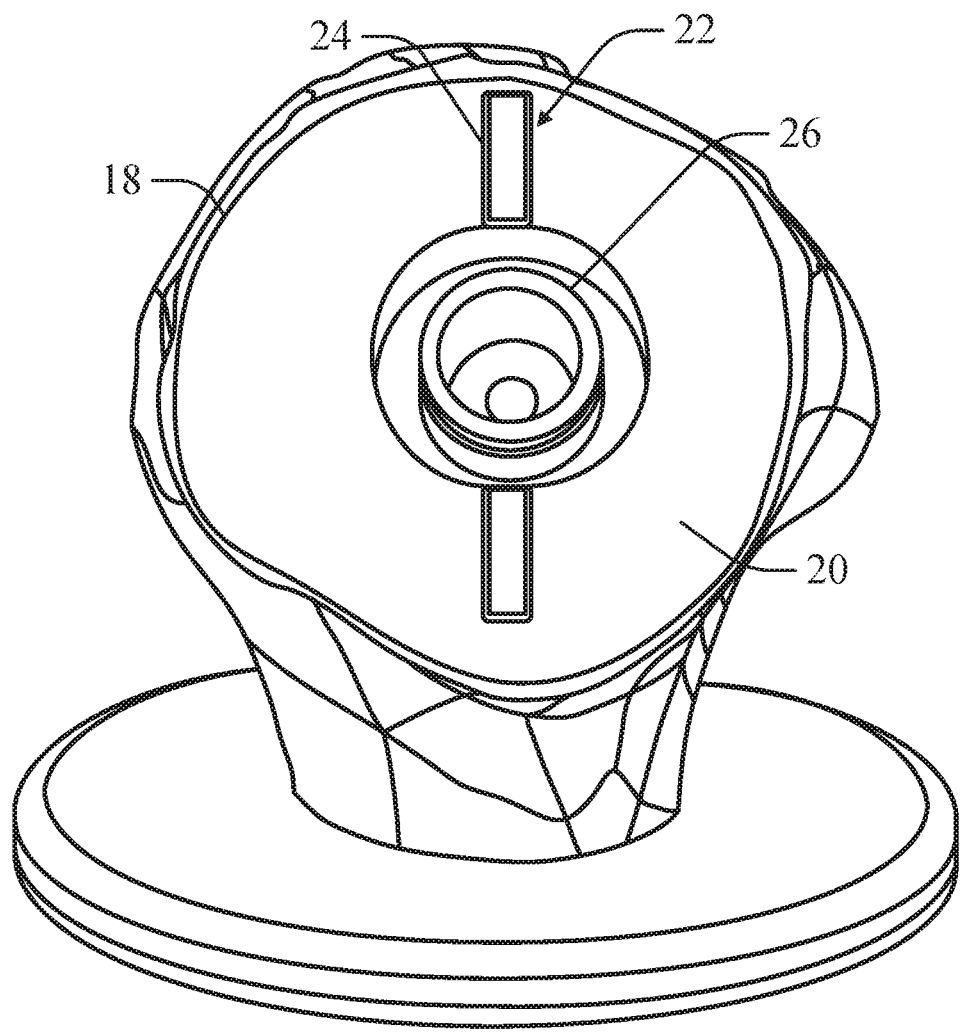
FIG. 3 is a front perspective view of a bone component according to an example of the present disclosure.

As depicted in FIGS. 1-3, in an example, the bone component 12 can include main body 18. In arthroplasty procedures in which the medical implant is positioned on a planar surface of the bone, the main body 18 can define a generally planar mounting surface 20. In at least one example, the main body 18 can be produced by 3D printing based on 3D scanning of the actual bone, such that the bone component 12 provides an accurate simulation of the shape and size of the actual bone.

Figure 6:
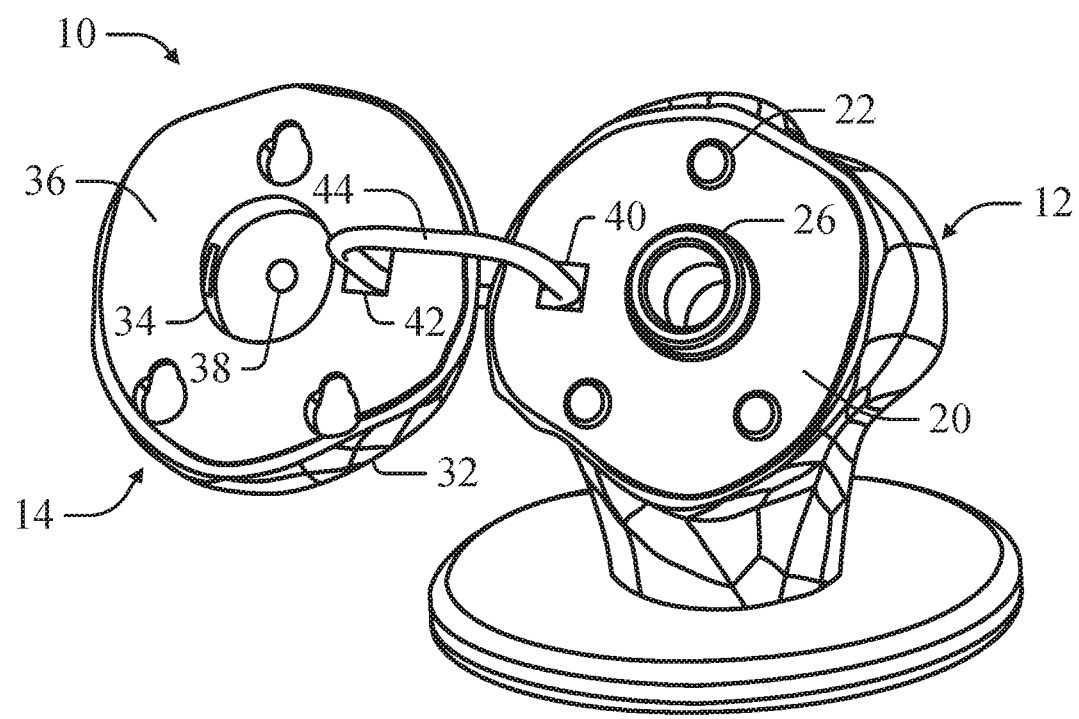
FIG. 6 is a front perspective view of a bone model according to an example of the present disclosure.

In an example, the main body 18 can include a positioning feature 22 that can be releasably engaged by the implant component 14 to position the implant component 14 on the mounting surface 20 as depicted in FIG. 6. In this configuration, the positioning feature 22 can maintain the positioning of the implant component 14 on the mounting surface 20 if the mounting surface 20 is angled. The positioning feature 22 can correspond to positioning features on the mounting surface of the mount implant.

In an example, the positioning feature 22 can have a slide 24 for slidably engaging the implant component 14 such that the implant component 14 can be slid on the positioning feature 22 and moved between at least an initial position and an offset position as depicted in FIG. 3. In this configuration, the implant component 14 can be slid on the bone component 12 at various offset positions such that the surgeon can trial offset positions for the implant component 14 to determine if offsetting the implant component 14 can improve the fit of the articulating surface 16. The surgeon can also determine if the mounting implant is properly mounted within the humerous.

In an example, the main body 18 can include a releasable locking feature 26 for releasably securing the implant component 14 to the bone component 12. The main body 18 can comprise a flexible, resilient material for releasably engaging the implant component 14. In at least one example, the releasable locking feature 26 can include a flexible, resilient nylon material.

In an example, the releasable locking feature 26 can be configured to engage an engagement feature of a head component. The head component can be attached to the medical implant itself, while the implant components can be simulated implant components for approximating sizing on the bone component 12. The engagement feature can comprise the locking pin opening through which a retention pin can be inserted for mounting the head component to the bone. In this configuration, the head component of the medical implant can be trialed directly on the bone component 12. In an example, the head component and bone component 12 can be provided as a surgical system or kit, where the head component can be disconnected from the bone component 12 during the operation after final trialing.

Figure 4:
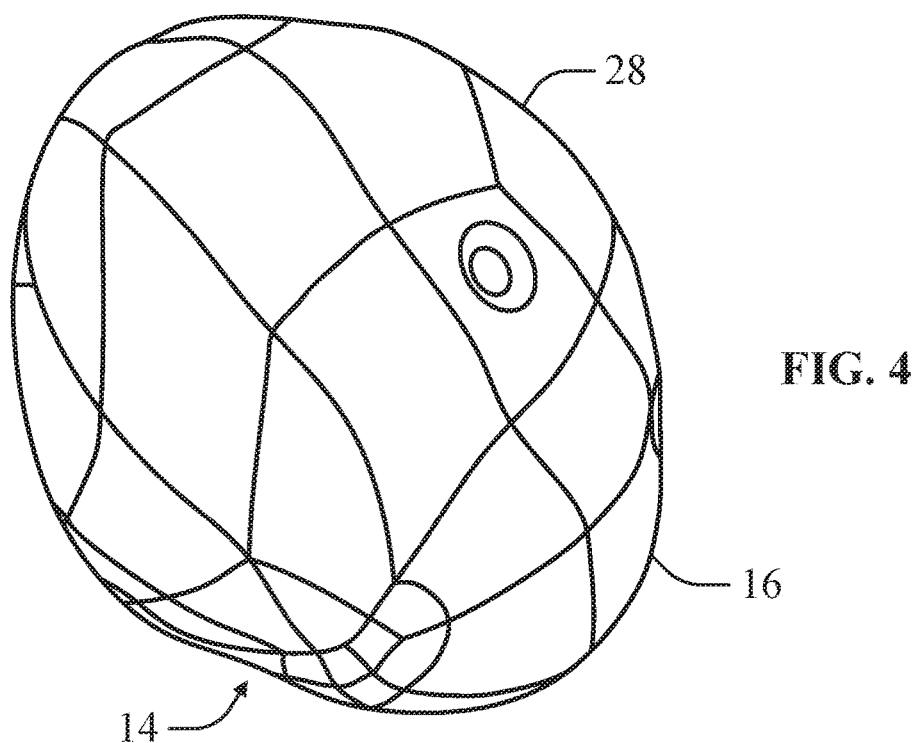
FIG. 4 is a front perspective view of an implant component according to an example of the present disclosure.
Figure 5:
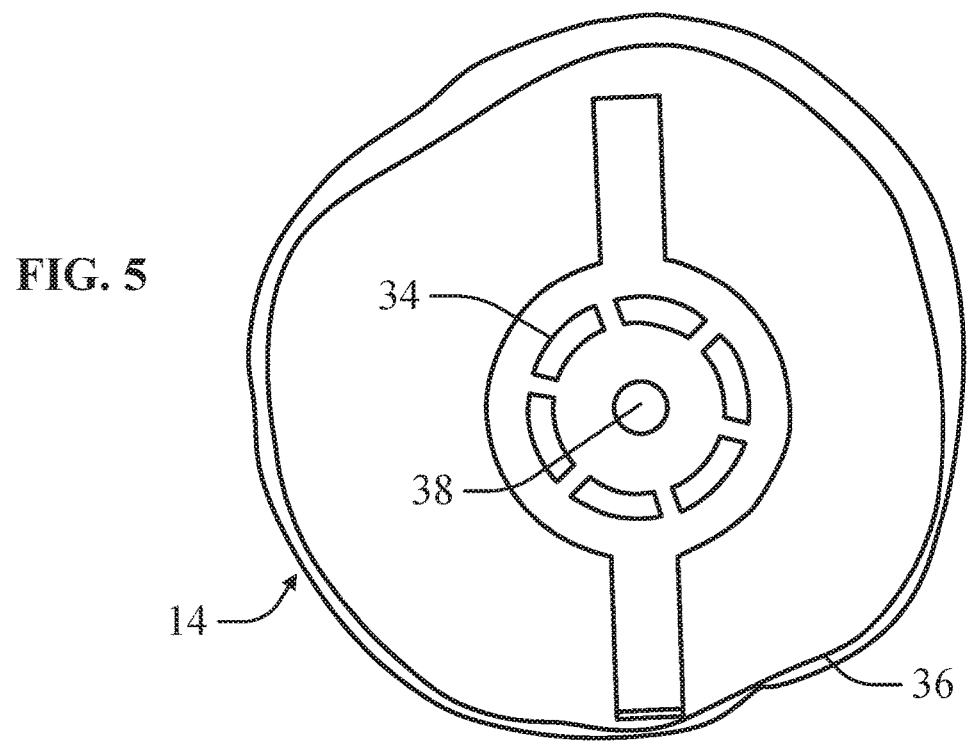
FIG. 5 is a rear view of the implant component depicted in FIG. 1 according to an example of the present disclosure.

As depicted in FIGS. 4-5, the implant component 14 can include an implant body 28 defining a simulated articulating surface 16. The implant component 14 can be sized and shaped to correspond to a head component of a medical implant such that the simulated articulating surface 16 accurately simulates the articulating surface of the head component. In at least one example, a plurality of implant components 14 can be provided, wherein each implant component 14 can be sized and shaped to correspond to a different head component allowing trialing of different head components.

In an example, the implant component 14 can be formed from an inexpensive material including, but not limited to injection molded polymers, 3D printed polymers and other inexpensive, low resiliency materials. Head components can comprise highly resilient materials for long term implantation within the body, which can be relatively expensive. By trialing of multiple implant components 14 that comprise of inexpensive materials, an accurate head component can subsequently be provided at a reduced cost.

In an example, the implant component 14 can comprise at least one alignment feature 32 for engaging the positioning feature 22 to align the implant component 14 on the bone component 12. The alignment feature 32 can slidably engage the positioning feature 22 allowing the implant component 14 to be positioned on the bone component 12 at various offset positions relative to the bone component 12. Offsetting the implant component 14 can allow the surgeon to determine if offsetting the head component on the bone will improve the fit of the medical implant.

Figure 7:
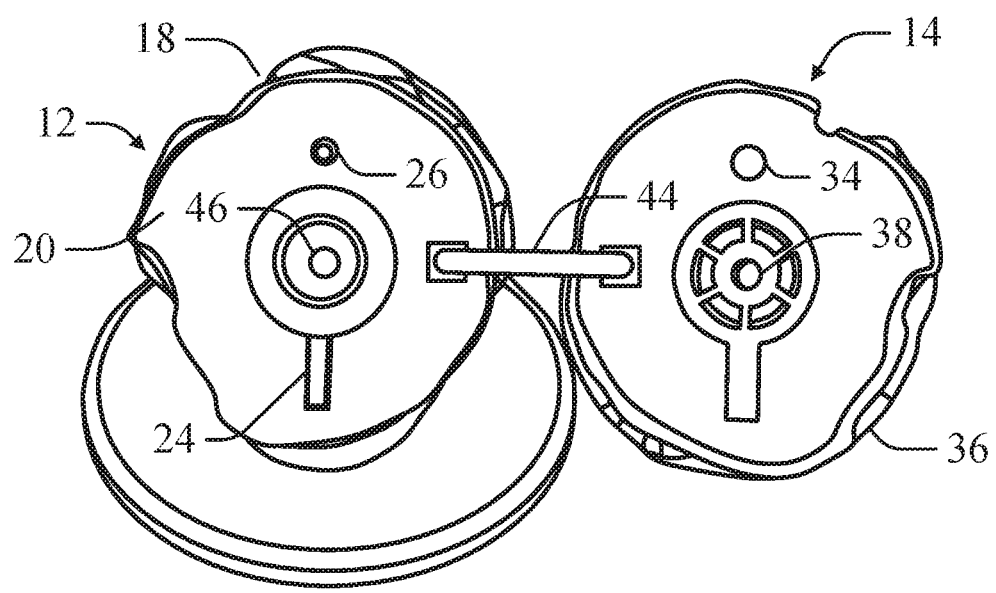
FIG. 7 is a front perspective view of a bone model according to an example of the present disclosure.
Figure 8:
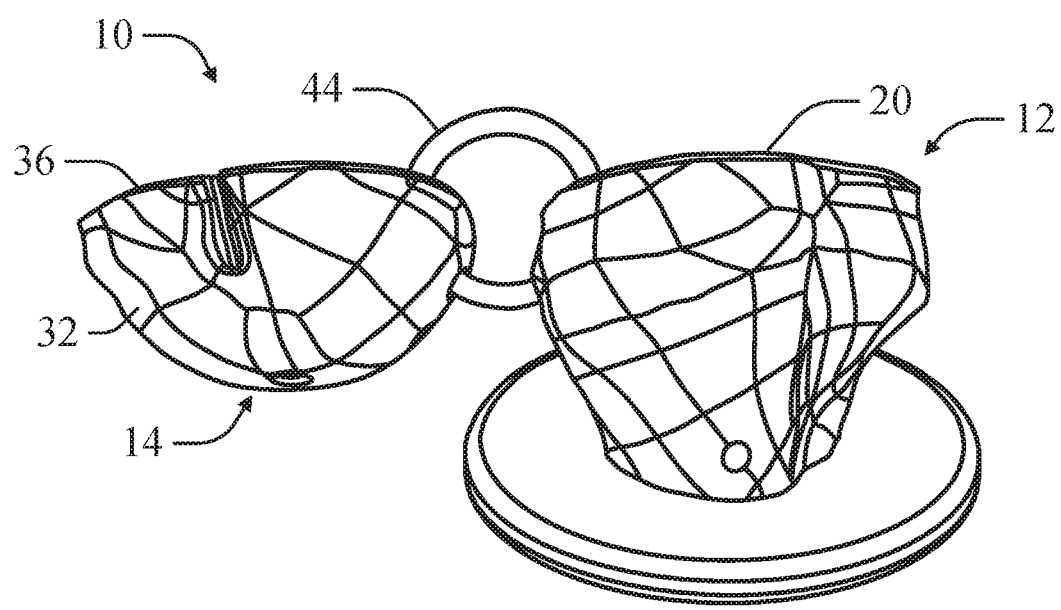
FIG. 8 is a rear view of the bone model depicted in FIG. 7 according to an example of the present disclosure.

In an example, the implant component 14 can comprise an engagement feature 34 that can engage the releasable locking feature 26 of the bone component 12 to mount the implant component 14 on the bone component 12. The implant component 14 can define a planar surface 36 opposite the articulating surface 16 of the implant component 14 that interfaces with the planar mounting surface 20 of the bone component 12. In at least one example, the implant component 14 can define a through hole 38, which simulates a locking pin port of a head component. In this configuration, the through hole 38 can simulate a guide hole in the head component through which a k-wire or other linear guide can be inserted. As depicted in FIGS. 7-8, in an example, the bone implant 12 can include a corresponding through hole 46 simulating a guide hole in the mount implant into which a k-wire or other linear guide can be inserted to guide engagement of the head implant onto the mount implant.

Figure 9:
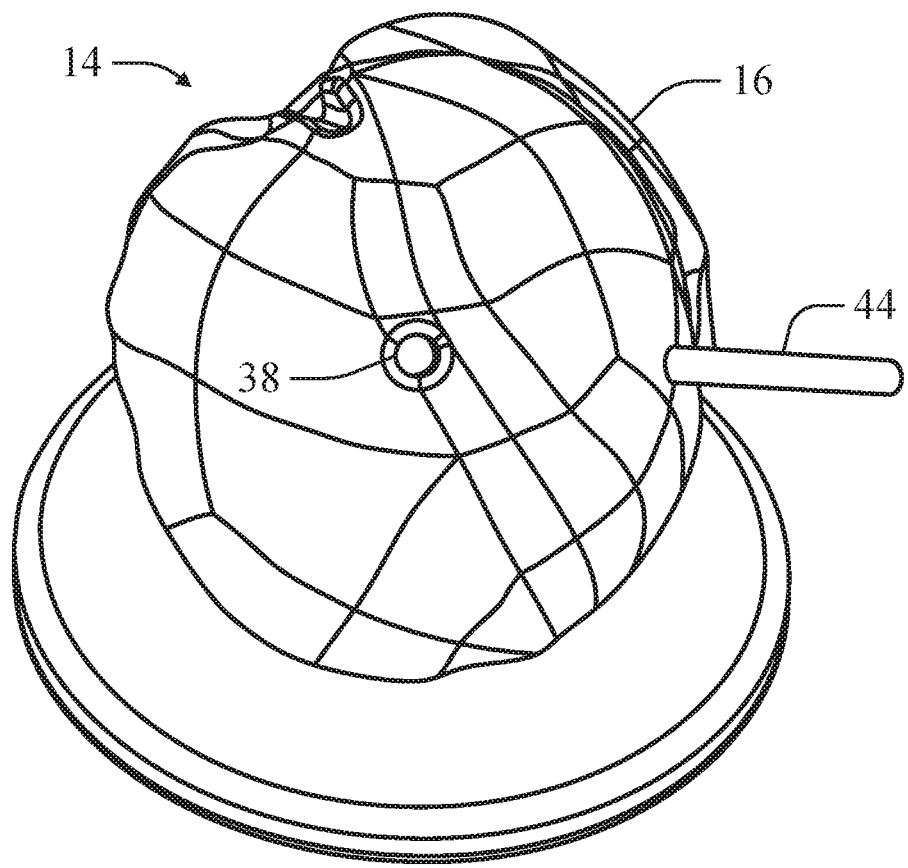
FIG. 9 is a front perspective view of the bone model depicted in FIG. 7 having an implant component fitted to the bone component according to an example of the present disclosure.

As depicted in FIGS. 6 and 9, in an example, the bone component 12 can further comprise a latch hole 40 and the implant component 14 can further comprise a corresponding latch hole 42. In this configuration, the bone model 10 can include a ring 44 insertable through the latch hole 40 of the bone component 12 and the latch hole 42 of the implant component 14. The ring 44 can be sized to permit the implant component 14 to be adjustably positioned on the bone component 14 to determine if an offset position for the implant component 14 provides an improved fit.

In an example, a method can be provided for trialing a medical implant having a head component defining an artificial articulating surface for repairing or replacing a natural articulating surface of a natural bone. The method can include providing a bone component 12 shaped to resemble the natural bone. The method can also include providing an implant component 14 defining an articulating surface 16, wherein the implant component 14 is sized and shaped such that the articulating surface 16 approximates the artificial articulating surface. The method can also include adjustably positioning the implant component 14 on the bone component 12 to determine the appropriate positioning and orientation of the artificial surface 16 of the implant component 14.

In an example, a method can be provided for trialing a medical implant for repairing or replacing a natural articulating surface of a natural bone. The method can include providing a bone component 12 shaped to resemble the natural bone. The method can also include providing a head component defining an articulating surface. The method can also include adjustably positioning the head component on the bone component 12 to determine the appropriate positioning and orientation of the artificial surface on the bone component 12 and corresponding the natural bone.

Various Notes & Examples

Example 1 is a bone model for trialing a medical implant having an artificial articulating surface and mountable on a natural bone to repair a natural articulating surface, comprising: a bone component shaped and sized to approximate the natural bone; and an implant component defining an artificial articulating surface and being sized and shaped such that the artificial articulating surface approximates the natural articulating surface; wherein the implant component is adjustably positioned on the bone component to approximate mounting of the medical implant onto the natural bone.

In Example 2, the bone model of Example 1 optionally includes, wherein the bone component defines a generally planar mounting surface; wherein the implant component is positionable on the planar mounting surface.

In Example 3, the bone model of Example 2 optionally includes, wherein the implant component defines a planar surface opposite the artificial articulating surface; wherein the planar surface of the implant component corresponds to the planar mounting surface of the bone component.

In Example 4, the bone model of any one of the preceding Examples, wherein the bone component further includes: at least one positioning feature for adjustably engaging the implant component to maintain the implant component on the bone component.

In Example 5, the bone model of Example 4 optionally includes, wherein the positioning feature further includes: a slide for slidably engaging the implant component such that the implant component can be slid on the at least one positioning feature to at least one offset position.

In Example 6, the bone model of any one or more of Examples 4-5 optionally include or 5, wherein the implant component further includes: at least one alignment feature for adjustably engaging the at least one positioning feature of the bone component.

In Example 7, the bone model of any one of the preceding Examples, wherein the bone component further includes a releasable locking feature engageable to the implant component for fixing the implant component on the bone component.

In Example 8, the bone model of Example 7 optionally includes, wherein the implant component further includes an engagement feature engageable to the releasable locking feature of the bone component.

In Example 9, the bone model of any one of the preceding Examples, wherein the bone component further includes: a bone latch hole; and a ring insertable through the bone latch hole.

In Example 10, the bone model of any one or more of Examples 8-9 optionally include, wherein the implant component further includes: an implant latch hole; wherein the ring is insertable through the implant latch hole to adjustably connect the implant component to the bone component.

Example 11 is a bone model system for trialing a medical implant mountable on a natural bone to repair a natural articulating surface, comprising: a bone component shaped and sized to approximate the natural bone; and a head component defining an artificial articulating surface and being sized and shaped such that the artificial articulating surface approximates the natural articulating surface, the head component, wherein the head component is adjustably positionable on the bone component to approximate mounting of the head component on the natural bone upon attachment of the head component to the medical implant In Example 12, the bone model system of Example 11 optionally includes, wherein the bone component defines a generally planar mounting surface; wherein the head component is positionable on the planar mounting surface.

In Example 13, the bone model system of Example 12 optionally includes, wherein the head component defines a planar surface opposite the artificial articulating surface; wherein the planar surface of the head component corresponds to the planar mounting surface of the bone component.

In Example 14, the bone model system of any one of the preceding Examples, wherein the bone component further includes: at least one positioning feature for adjustably engaging the bone component to maintain the head component on the bone component.

In Example 15, the bone model system of Example 14 optionally includes, wherein the positioning feature further includes: a slide for slidably engaging the bone component such that the head component can be slid on the at least one positioning feature to at least one offset position.

In Example 16, the bone model system of any one or more of Examples 14-15 optionally include or 15, wherein the head component further includes: at least one alignment feature for adjustably engaging the at least one positioning feature of the bone component.

In Example 17, the bone model system of any one of the preceding Examples, the bone component further including a releasable locking feature engageable to the head component to secure the head component to the bone component.

In Example 18, the bone model system of Example 17 optionally includes, wherein the head component further includes an engagement feature engageable to the releasable locking feature of the bone component; wherein the engagement feature is engageable to a mounting feature of the head component.

In Example 19, the bone model system of any one of the preceding Examples, the head component further comprising a locking pin port for receiving a locking pin to mount the head component to the medical implant.

Example 20 is a method for trialing a medical implant, comprising: providing a bone component shaped and sized to approximate a natural bone to which the medical implant is mountable; providing an implant component defining an artificial articulating surface; adjustably positioning the implant component on the bone component to approximate positioning of the medical implant on the natural bone.

In Example 21, the method of Example 20 optionally includes, wherein the implant component is sized and shaped to approximate a head component attachable to the medical implant; wherein the head component defines an articulating surface approximated by the artificial articulating surface.

In Example 22, the method of any one or more of Examples 20-21 optionally include and 21, wherein the bone component defines a generally planar mounting surface.

In Example 23, the method of Example 22 optionally includes adjustably positioning the implant component on the bone component comprises positioning the implant component on the planar mounting surface to simulate positioning of the medical component on the natural bone.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A bone model for trialing a medical implant mountable on a natural bone to repair a natural articulating surface, comprising:
    a bone component shaped and sized to approximate at least a portion of the natural bone, the bone component comprising a physical bone model that is manufactured based on measurements obtained by imaging the natural bone; and
    a trial implant component shaped and sized to approximate at least a portion of the medical implant, the trial implant component including a trial articulating surface that approximates an articulating surface of the medical implant;
    wherein the trial implant component is positionable on the bone component to approximate mounting of the medical implant onto the natural bone; and
    wherein the bone component further includes a releasable locking feature engageable to the trial implant component for fixing the trial implant component on the bone component.

2. The bone model of claim 1, wherein the bone component defines a generally planar mounting surface;
    wherein the trial implant component is positionable on the planar mounting surface.

3. The bone model of claim 2, wherein the trial implant component defines a planar surface opposite the artificial articulating surface;
    wherein the planar surface of the trial implant component is shaped to correspond to the planar mounting surface of the bone component.

4. The bone model of claim 1, wherein the bone component further includes:
    at least one positioning feature for adjustably engaging the trial implant component to maintain the trial implant component on the bone component.

5. The bone model of claim 4, wherein the positioning feature further includes:
    a slide for slidably engaging the trial implant component such that the trial implant component can be slid on the at least one positioning feature to at least one offset position.

6. The bone model of claim 4, wherein the trial implant component further includes:
    at least one alignment feature for adjustably engaging the at least one positioning feature of the bone component.

7. The bone model of claim 1, wherein the trial implant component further includes an engagement feature engageable to the releasable locking feature of the bone component.

8. The bone model of claim 1, wherein the bone component further includes:
    a bone latch hole; and
    a ring insertable through the bone latch hole.

9. The bone model of claim 8, wherein the trial implant component further includes:
    an implant latch hole;
    wherein the ring is insertable through the implant latch hole to adjustably connect the implant component to the bone component.

10. The bone model of claim 1, wherein the bone component manufactured by 3D printing.

11. A bone model for trialing a medical implant mountable on a natural bone to repair a natural articulating surface, comprising:
    a bone component shaped and sized to approximate at least a portion of the natural bone, the bone component manufactured based on measurements obtained by imaging the natural bone; and
    a trial implant component shaped and sized to approximate at least a portion of the medical implant, the trial implant component including a trial articulating surface that approximates an articulating surface of the medical implant;
    wherein the trial implant component is positionable on the bone component to approximate mounting of the medical implant onto the natural bone; and
    wherein the bone component further includes a releasable locking feature engageable to the trial implant component for fixing the trial implant component on the bone component and at least one positioning feature for adjustably engaging the trial implant component to maintain the trial implant component on the bone component, wherein the positioning feature further includes a slide for slidably engaging the trial implant component such that the trial implant component can be slid on the at least one positioning feature to at least one offset position.

12. The bone model of claim 11, wherein the bone component is manufactured by 3D printing.

13. A bone model for trialing a medical implant mountable on a natural bone to repair a natural articulating surface, comprising:
    a bone component shaped and sized to approximate at least a portion of the natural bone, the bone component manufactured based on measurements obtained by imaging the natural bone; and
    a trial implant component shaped and sized to approximate at least a portion of the medical implant, the trial implant component including a trial articulating surface that approximates an articulating surface of the medical implant;
    wherein the trial implant component is positionable on the bone component to approximate mounting of the medical implant onto the natural bone; and
    wherein the bone component further includes a releasable locking feature engageable to the trial implant component for fixing the trial implant component on the bone component, a bone latch hole, and a ring insertable through the bone latch hole.

14. The bone model of claim 13, wherein the bone component defines a generally planar mounting surface;
    wherein the trial implant component is positionable on the planar mounting surface.

15. The bone model of claim 14, wherein the trial implant component defines a planar surface opposite the trial articulating surface;
    wherein the planar surface of the trial implant component corresponds to the planar mounting surface of the bone component.

16. The bone model of claim 15, wherein the bone component further includes:
    at least one positioning feature for adjustably engaging the bone component to maintain the trial implant component on the bone component.

17. The bone model of claim 16, wherein the positioning feature further includes:
    a slide for slidably engaging the bone component such that the trial implant component can be slid on the at least one positioning feature to at least one offset position.

18. The bone model of claim 17, wherein the trial implant component further includes:
  at least one alignment feature for adjustably engaging the at least one positioning feature of the bone component.

19. The bone model of claim 13, wherein the bone component is manufactured by 3D printing.

\* \* \* \* \*